US011308627B1

United States Patent
Alsaggaf et al.

(10) Patent No.: US 11,308,627 B1
(45) Date of Patent: Apr. 19, 2022

(54) METHOD FOR 3D ULTRASOUND RECONSTRUCTION OF SUPRASPINATUS (SSP) TENDON

(71) Applicant: King Abdulaziz University, Jeddah (SA)

(72) Inventors: Mohammed U. Alsaggaf, Jeddah (SA); Irraivan Elamvazuthi, Ipoh (MY); Ubaid M. Al-Saggaf, Jeddah (SA); Muhammad Moinuddin, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/478,332

(22) Filed: Sep. 17, 2021

(51) Int. Cl.
*G06K 9/00* (2022.01)
*G06T 7/155* (2017.01)
*G06T 7/30* (2017.01)
*G06T 17/20* (2006.01)

(52) U.S. Cl.
CPC .............. *G06T 7/155* (2017.01); *G06T 7/30* (2017.01); *G06T 17/205* (2013.01); *G06T 2207/10136* (2013.01); *G06T 2207/20004* (2013.01); *G06T 2207/20032* (2013.01); *G06T 2207/20092* (2013.01); *G06T 2207/30004* (2013.01)

(58) Field of Classification Search
CPC .................. G06T 7/0012; G06T 17/00; G06T 2210/41; G06T 15/00; G06T 2207/10132; G06T 2200/04
See application file for complete search history.

(56) References Cited

U.S. PATENT DOCUMENTS

| 7,141,020 B2 | 11/2006 | Poland et al. |
| 7,302,286 B2 | 11/2007 | Camus et al. |
| 7,526,113 B2 | 4/2009 | Jacob et al. |

(Continued)

OTHER PUBLICATIONS

Gupta, et al., Curvelet based automatic segmentation of supraspinatus tendon from ultrasound image: a focused assistive diagnostic method, Biomedical Engineering Online, vol. 13, Article No. 157, Dec. 4, 2014, pp. 1-18, AAPA furnished via IDS.*

(Continued)

*Primary Examiner* — Guillermo M Rivera-Martinez
(74) *Attorney, Agent, or Firm* — Oblon, McClelland, Maier & Neustadt, L.L.P.

(57) ABSTRACT

A device, method, and non-transitory computer readable medium for interactive 3D visualization of ultrasound images of a supraspinatus tendon injury. Ultrasound images are acquired of a region in which the supraspinatus tendon injury is suspected. The ultrasound images are preprocessed, and energy of the preprocessed ultrasound images is minimized. A set of supraspinatus tendon images are extracted from low energy preprocessed ultrasound images. A morphological operation is performed on the set of supraspinatus tendon images to generate a smoothed set of supraspinatus tendon images. A binary mask is applied to the smoothed set of supraspinatus tendon images to detect boundary points of the supraspinatus tendon and generate a set of segmented image frames. The set of segmented image frames are arranged based on spatial position of each segmented image frame with respect to the supraspinatus tendon. A 3D representation of the supraspinatus tendon is reconstructed and rendered on a display.

20 Claims, 8 Drawing Sheets

(56) References Cited

U.S. PATENT DOCUMENTS

| | | | |
|---|---|---|---|
| 7,988,632 B2 | 8/2011 | Yao et al. | |
| 9,700,284 B2 | 7/2017 | Kapoor et al. | |
| 10,242,450 B2 | 3/2019 | Prevost et al. | |
| 10,713,802 B2 | 7/2020 | Cong et al. | |
| 10,867,436 B2 | 12/2020 | Oved | |
| 2011/0134113 A1* | 6/2011 | Ma | A61B 8/4245 |
| | | | 345/419 |
| 2012/0004553 A1* | 1/2012 | Kanayama | G01S 15/8995 |
| | | | 600/443 |
| 2015/0238164 A1* | 8/2015 | Cho | A61B 8/5215 |
| | | | 600/439 |
| 2018/0214172 A1* | 8/2018 | Donnelly | A61B 8/12 |
| 2020/0129139 A1 | 4/2020 | Faghih et al. | |
| 2020/0167911 A1* | 5/2020 | Park | G06N 3/02 |

OTHER PUBLICATIONS

Rishu Gupta, et al., "Curvelet based automatic segmentation of supraspinatus tendon from ultrasound image: a focused assistive diagnostic method", Biomedical Engineering Online, vol. 13, Article No: 157, Dec. 4, 2014, pp. 1-18.

* cited by examiner

METHOD FOR 3D ULTRASOUND RECONSTRUCTION OF SUPRASPINATUS (SSP) TENDON

BACKGROUND

Technical Field

The present disclosure is directed to 3D ultrasound reconstruction of a supraspinatus (SSP) tendon.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The musculoskeletal (MSK) system in the human body encapsulates bones, muscles, ligaments, joints, and other connective tissues, which provides support, stability, and movement to the human body. The shoulder is an integral part of the human body for almost all upper body motion activities. The rotator cuff in the shoulder provides flexibility and strength to the shoulder with the help of a complex network of tendons from four separate muscles, which include the 1) Supraspinatus (SSP), 2) Infraspinatus, 3) Teres minor, and 4) Subscapularis. The tendons and ligaments tend to have degenerative nature, which leads them to wear out with age, thus affecting daily life activities. Shoulder problems due to tendon weariness are common after the age of 40 years, but they may be non-existent before 30 years. The weariness of tendon induces pathological conditions. A shoulder injury may cause pain, and even a minor injury may take as long as three to four weeks for recovery. Of all the tendons in the rotator cuff, the SSP tendon is most susceptible to pathology.

The SSP tendon is a small and weak muscle, around 25 millimeters in length and about the 12 millimeters in thickness. The anatomical position of the SSP tendon (suppressed between the acromion and the coracohumeral ligament and connecting the under surface of anterior acromion and coracoid process) makes it highly susceptible to risk of attrition and compression.

Disorders of the SSP tendon are presently diagnosed based on patient history, physical examination, and radiological imaging, such as ultrasound imaging, magnetic resonance imaging (MRI), and other imaging modalities. Generally, ultrasound imaging is preferred as a screening imaging modality due to its special features, such as real-time motion pictures and videos, patient acceptability rate, use of non-ionizing radiations, highly economical, and portability. Such features are non-existent in other imaging modalities such as MRI. However, ultrasound imaging has limitations, such as existing artifacts, contrast, low image resolution, limited views, and inaccurate volume visualization. Diagnosing SSP tendon disorders (or pathologies) using ultrasound images is challenging due to these limitations. Diagnostics using ultrasound imaging modality essentially depends upon the expertise of sonographers and radiologists.

Various studies have been carried out in recent years to estimate the thickness and cross-section area of the SSP tendon and to understand biomechanical properties and muscle kinematics of the SSP tendon with the help of two dimensional (2D) ultrasound images. The SSP tendon disorders diagnosed using 2D ultrasound images result in limited interpretation by radiologists and doctors. The known methods that use 2D ultrasound imaging systems have failed to provide an optimal solution for combining image processing algorithms and ultrasound imaging system to provide three-dimensional (3D) visualization of the SSP tendon and an automatic diagnostic tool for automatic segmentation and analysis of the SSP tendon. The 3D visualization and automatic segmentation and analysis will assist in providing more accurate diagnoses of the disorders in the SSP tendon.

Various solutions have been developed in recent years for diagnosing disorders using ultrasound imaging. An image processing framework that facilitates automated ovarian follicular monitoring for real-time use in clinical practice and home-based monitoring was described in US20200129139A1, "System and Method for Automated Ovarian Follicular Monitoring", incorporated herein by reference in its entirety. However, this reference does not disclose 3D visualization of ultrasound images.

An ultrasound imaging system for inspecting an object in a volume by conducting segmentation of the object simultaneously out of a 3D ultrasound image data and contrast-enhanced 3D ultrasound image data was described in U.S. Ser. No. 10/242,450B2, "Coupled segmentation in 3D conventional ultrasound and contrast-enhanced ultrasound images", incorporated herein by reference in its entirety. However, this reference does not disclose applying morphological and smoothing operations on preprocessed ultrasound images, thus suffers from distortion.

An ultrasound image processing system to segment a target area according to any one group of 3D image data of multiple sets of 3D image data of a same target tissue to obtain a boundary of the target area and map the boundary to other sets of 3D image data according to the spatial mapping relationship between the multiple sets of three-dimensional image data was described in U.S. Ser. No. 10/713,802B2, "Ultrasonic image processing system and method and device thereof, ultrasonic diagnostic device", incorporated herein by reference in its entirety. However, this reference differs from the present disclosure in that a 3D representation of the supraspinatus tendonis not reconstructed by forming a 3D mesh of segmented images.

Further, automatic segmentation of an SSP tendon ultrasound image by combining curvelet transform and mathematical concepts of logical and morphological operators along with area filtering have been described. (See: Rishu Gupta, Irraivan Elamvazuthi, Sarat Chandra Dass, Ibrahima Faye, Pandian Vasant, John George, and Faizatul Izza, "Curvelet based automatic segmentation of supraspinatus tendon from ultrasound image: a focused assistive diagnostic method", BioMedical Engineering OnLine, volume 13, Article number: 157 (2014), DOI: 10.1186/1475-925X-13-157, incorporated herein by reference in its entirety). However, this reference does not arrange segmented images based on their spatial position with respect to supraspinatus tendon and reconstruct 3D representation of the supraspinatus tendon by forming a 3D mesh of the segmented images.

Each of the aforementioned references suffers from one or more drawbacks hindering their adoption. Accordingly, it is one object of the present disclosure to provide methods and systems for 3D reconstruction of ultrasound images of the SSP tendon which improve the quality of the 3D representation. The present disclosure focuses on automatic segmentation of the SSP tendon from ultrasound images to automate diagnosis of disorders in the SSP tendon using the 3D reconstruction.

SUMMARY

In an exemplary embodiment, a system for interactive 3D visualization of ultrasound images of a supraspinatus tendon injury is disclosed. The system includes a high frequency ultrasound probe, a database, a display, and a computing device. The high frequency ultrasound probe is configured to image a region in which the supraspinatus tendon injury is suspected, and generate a plurality of ultrasound images composed of pixels. The database is configured to store the plurality of ultrasound images. The computing device is operatively connected to the database and the display. The computing device includes circuitry and a non-transitory computer readable medium having instructions stored therein. The instructions are executed by one or more processors to: acquire the plurality of ultrasound images from the database; preprocess the plurality of ultrasound images to generate a plurality of preprocessed ultrasound images; minimize an energy of the plurality of preprocessed ultrasound images to generate a plurality of low energy preprocessed ultrasound images; extract, from the plurality of low energy preprocessed ultrasound images, a set of supraspinatus tendon images; perform a morphological operation on the set of supraspinatus tendon images to generate a smoothed set of supraspinatus tendon images; apply a binary mask to the smoothed set of supraspinatus tendon images to detect boundary points of the supraspinatus tendon to generate a set of segmented image frames; arrange the set of segmented image frames based on a spatial position of each segmented image frame with respect to the supraspinatus tendon; reconstruct a 3D representation of the supraspinatus tendon; and render the 3D representation of the supraspinatus tendon on the display.

In another exemplary embodiment, a method for interactive 3D visualization of ultrasound images of a supraspinatus tendon injury is disclosed. The method includes acquiring a plurality of ultrasound images of a region in which the supraspinatus tendon injury is suspected. The method further includes preprocessing the plurality of ultrasound images to generate a plurality of preprocessed ultrasound images composed of pixels. The method further includes minimizing an energy of the plurality of preprocessed ultrasound images to generate a plurality of low energy preprocessed ultrasound images. The method further includes extracting, from the plurality of low energy preprocessed ultrasound images, a set of supraspinatus tendon images. The method further includes performing a morphological operation on the set of supraspinatus tendon images to generate a smoothed set of supraspinatus tendon images. The method further includes applying a binary mask to the smoothed set of supraspinatus tendon images to detect boundary points of the supraspinatus tendon to generate a set of segmented image frames. The method further includes arranging the set of segmented image frames based on a spatial position of each segmented image frame with respect to the supraspinatus tendon. The method further includes reconstructing a 3D representation of the supraspinatus tendon and rendering the 3D representation of the supraspinatus tendon on a display.

In another exemplary embodiment, a method for interactive 3D visualization of ultrasound images of a supraspinatus tendon injury is disclosed. The method includes acquiring a plurality of ultrasound images of a region in which the supraspinatus tendon injury is suspected by isolating a shoulder region in which the supraspinatus tendon injury is suspected, imaging the shoulder region by a high frequency ultrasound probe, and storing a plurality of timestamped ultrasound images composed of pixels. The method further includes preprocessing the plurality of ultrasound images by applying statistically adaptive contrast enhancement and speckle removal, thus generating a plurality of preprocessed ultrasound images. The method further includes minimizing an energy of the plurality of preprocessed ultrasound images by applying an evolutionary algorithm to generate a plurality of low energy preprocessed ultrasound images. The evolutionary algorithm is a Darwinian particle swarm optimization. The method further includes extracting, from the plurality of low energy preprocessed ultrasound images, a set of supraspinatus tendon images by applying a segmentation algorithm. The segmentation algorithm is an enhanced Chan-Vese algorithm. The method further includes performing a morphological operation on the set of supraspinatus tendon images to generate a smoothed set of supraspinatus tendon images. The method further includes applying a binary mask to the smoothed set of supraspinatus tendon images to detect boundary points of the supraspinatus tendon by setting the pixels in the smoothed set of supraspinatus tendon images to zero when a corresponding pixel in the binary mask is zero and detecting boundary points by comparing each remaining pixel to an edge point of the binary mask, thus generating a set of segmented image frames. The method further includes arranging the set of segmented image frames based on a spatial position of each segmented image frame with respect to the supraspinatus tendon by image registration. The method further includes reconstructing a 3D representation of the supraspinatus tendon by applying an enhanced marching cubes operation on the set of segmented image frames to remove duplicate vertices and smooth surface and boundaries to generate an enhanced set of segmented image frames, forming a 3D mesh of the enhanced set of segmented images, and forming a patched 3D mesh by filling in open areas of the 3D mesh with pixels having an intensity equal to that of a neighboring pixel. The method further includes rendering the 3D representation of the supraspinatus tendon on a display.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
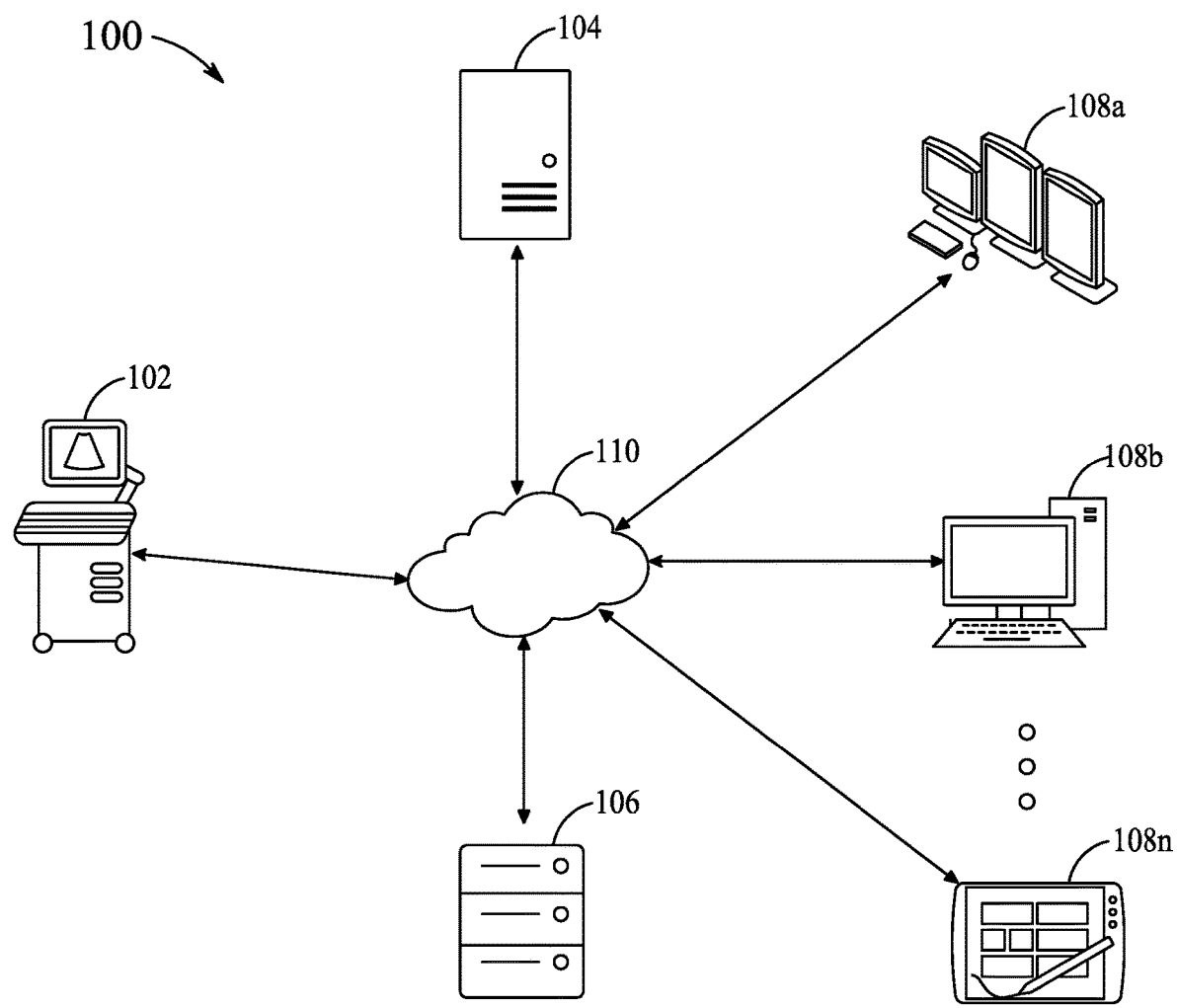
FIG. 1 depicts a network architecture of an ultrasound imaging system, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Medical imaging refers to techniques and processes of imaging the interior of a body (for example, a human body) to diagnose, monitor, or treat medical conditions and to visually represent functions of one or more organs or tissues in the body. Medical ultrasound imaging or sonography refers to a medical imaging technique that uses high-frequency sound waves for imaging internal body structures such as tendons, muscles, joints, blood vessels, tissues, and internal organs. Medical ultrasound images, also known as sonograms, are created by sending pulses of ultrasound into the body using a probe (or a transducer). The ultrasound pulses echo off tissues with different reflection properties and are returned to the probe which records and displays them as an image. Ultrasound images can be captured in real-time and thus, can be used to show movement of the body's internal organs as well as blood flowing through the blood vessels.

The human body consists of four basic tissues in the form of nervous, muscular, epithelial, and connective tissues (tendons, fat, and bones). One of the primary purposes of muscular and connective tissues is to enable mechanical functionality of any movement in the body and thus are highly prone to injuries and disorders. Shoulder pain is a common disorder among musculoskeletal (MSK) disorders that occur in bones, ligaments, tendons, and other soft tissues around joints. Pathology (or disorders) within the SSP tendon includes, but is not limited to, a tear of the tendon, tendinosis (collagenous degeneration of the tendon), tendinitis (inflammation of the tendon), and tendon impingement.

Aspects of this disclosure are directed to a system, device, and method for interactive three dimensional (3D) visualization of supraspinatus (SSP) tendon injuries in ultrasound images through segmentation and 3D reconstruction. The present disclosure discloses preprocessing a plurality of ultrasound images of a region in which the SSP tendon injury is suspected and minimizing an energy of a plurality of preprocessed ultrasound images. A set of SSP tendon images are extracted from a plurality of low energy preprocessed ultrasound images. A morphological operation is performed on the set of SSP tendon images to generate a smoothed set of SSP tendon images. A binary mask is applied to the smoothed set of SSP tendon images to generate a set of segmented image frames. The set of segmented image frames are arranged based on a spatial position of each segmented image frame with respect to the SSP tendon. A 3D representation of the SSP tendon is reconstructed and rendered on a display.

FIG. 1 depicts a network architecture of an ultrasound imaging system 100, according to exemplary aspects of the present disclosure.

According to aspects of the present disclosure, the ultrasound imaging system 100 includes an ultrasound imaging device 102, a medical imaging system 104, a storage device 106, one or more display devices 108a-108n (also generally referred to as display device(s) 108), and a network 110.

The ultrasound imaging device 102 generates ultrasound images of one or more of tendons, muscles, joints, blood vessels, tissues, and internal organs of a body. The ultrasound imaging device 102 includes a high frequency ultrasound probe (or a transducer) to image a region in the body. In an aspect of the present disclosure, the high frequency ultrasound probe may be used to image the SSP tendon in shoulder region of the body.

In the human body, the SSP tendon is a superficial structure of tissue close to the skin. The ultrasound imaging device 102 may perform ultrasound imaging of the SSP tendon using the high frequency ultrasound probe. In an aspect of the present disclosure, the high frequency ultrasound probe may be a linear probe capable of imaging at high frequencies. For example, the high frequency ultrasound probe may perform ultrasound imaging in the frequency range of 7-8 MHz. The ultrasound imaging device 102 receives the sound reflected from the SSP tendon and generates a plurality of ultrasound images of the SSP tendon. A physician, radiologist, or a technician may press the high frequency ultrasound probe against the skin on a region of a patient's body to generate the plurality of ultrasound images. In an aspect of the present disclosure, the plurality of ultrasound images may be timestamped, i.e., image file corresponding to each of the plurality of ultrasound images includes a timestamp. The timestamp of an ultrasound image includes date and/or time at which the ultrasound image was generated. In an aspect of the present disclosure, the region of the patient's body may correspond to the region around the SSP tendon.

The medical imaging system 104 acquires the plurality of ultrasound images from the ultrasound imaging device 102 via the network 110. The medical imaging system 104 may archive (or store) the plurality of ultrasound images in the storage device 106. In an aspect of the present disclosure, the ultrasound imaging device 102 transmits the plurality of ultrasound images to the storage device 106 and the medical imaging system 104 acquires the plurality of ultrasound images from the storage device 106. The medical imaging system 104 performs one or more image processing techniques or algorithm to process the plurality of ultrasound images. The medical imaging system 104 processes the plurality of ultrasound images for segmentation and 3D reconstruction of the plurality of ultrasound images to generate the 3D representation of the SSP tendon. The medical imaging system 104 may store the 3D representation of the SSP tendon in the storage device 106. In an aspect of the present disclosure, the medical imaging system 104 may include a computer program or an application, such as an enterprise imaging software to optimally capture, index, manage, archive, store, distribute, view, exchange, process, and analyze the plurality of ultrasound images.

The storage device 106 stores the plurality of ultrasound images. The storage device 106 receives the plurality of ultrasound images directly from the ultrasound imaging device 102 or via the medical imaging system 104. In an aspect of the present disclosure, the storage device 106 may store the plurality of ultrasound images generated by the ultrasound imaging device 102 or processed ultrasound images generated as a result of processing performed by the medical imaging system 104. The plurality of ultrasound images may be stored along with their corresponding timestamp. In an aspect of the present disclosure, the storage device 106 may include a database. The plurality of ultrasound images may be stored in the database.

In an aspect of the present disclosure, the storage device 106 may store a plurality of patient records. Each of the plurality of patient records may correspond to a patient and include one or more of: patient's personal information, doctor's prescription, diagnostic reports, patient's medical history, ultrasound images of the patient generated by the ultrasound imaging device 102, and medical images of the patient generated by other medical imaging modalities, such as X-ray machine, magnetic resonance imaging (Mill) machine, computed tomography (CT) machine, and positron emission tomography (PET) machine.

The storage device 106 may be implemented using one or more digital storage technologies such as, direct-attached storage (DAS), network attached storage (NAS), storage area network (SAN), hard disk drives (HDD), solid-state drives (SSD), optical storage devices, and flash drives.

The display devices 108 correspond to one or more devices that display the plurality of ultrasound images and/or the 3D representation of the SSP tendon generated by processing the plurality of ultrasound images. The display devices 108 may correspond to the display device 108a of a computing workstation of a radiologist, the display device 108b of a computing device associated with a doctor, or the display device 108n of any other mobile computing device. The display devices 108 may access the network 110 to retrieve the plurality of ultrasound images and/or the 3D representation of the SSP tendon from the ultrasound imaging device 102, the medical imaging system 104, and the storage device 106. A user of the display devices 108, such as the radiologist, the doctor, or any other user may analyze the 3D representation of the SSP tendon displayed on the display device 108 to diagnose one or more disorders related to the SSP tendon.

The network 110 can be a public network, such as the Internet, or a private network such as an LAN or WAN network, or any combination thereof and can also include PSTN or ISDN sub-networks. The network 110 can also be wired, such as an Ethernet network, or can be wireless such as a cellular network including EDGE, 3G, 4G, and 5G wireless cellular systems. The wireless network can also be WiFi, Bluetooth, or any other wireless form of communication that is known. The ultrasound imaging device 102, the medical imaging system 104, the storage device 106, and the display devices 108 communicate with each other via the network 110.

Figure 2:
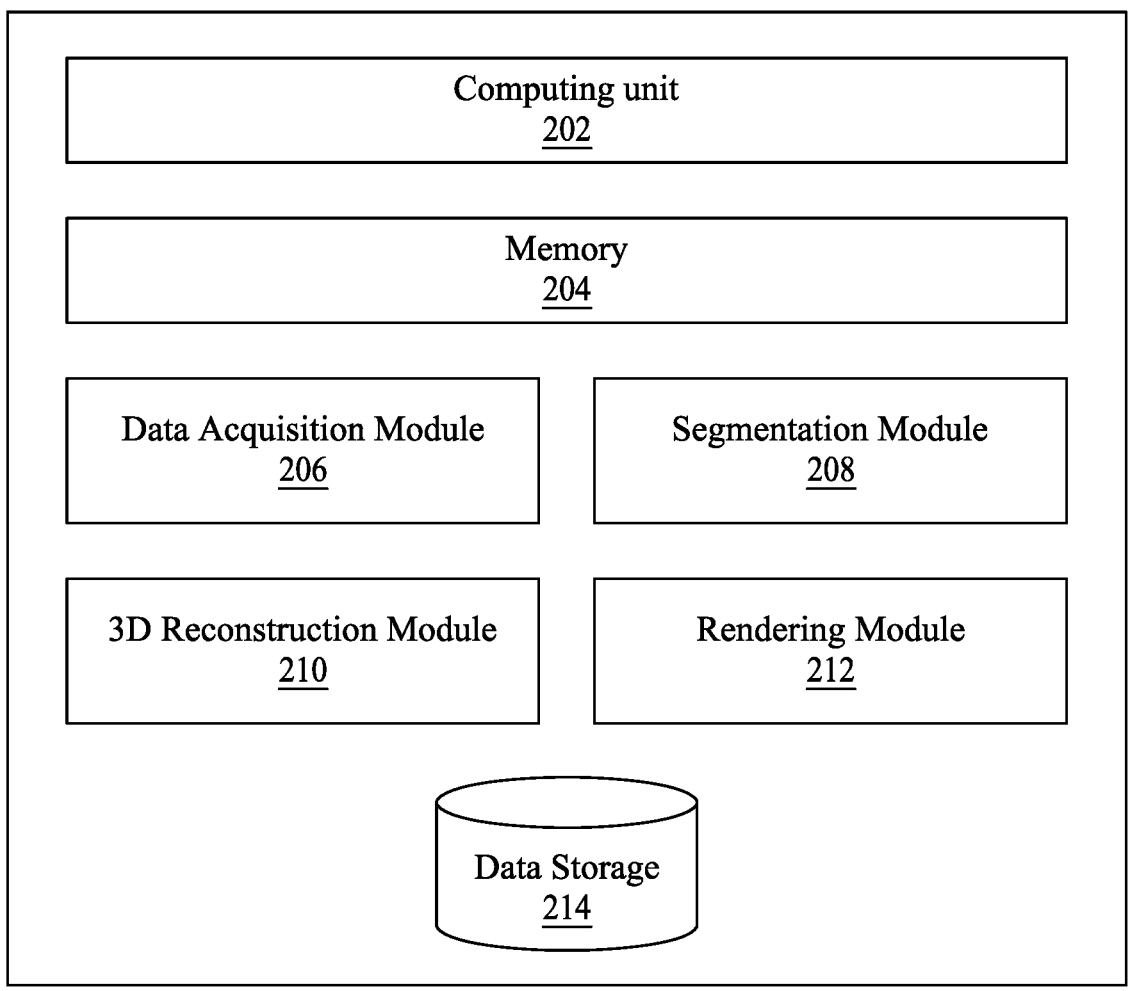
FIG. 2 depicts a schematic diagram of a computing device used to perform the image reconstruction, according to certain embodiments.

FIG. 2 depicts a block diagram of a computing device 200 which constructs the ultrasound image according to exemplary aspects of the present disclosure.

According to aspects of the present disclosure, the computing device 200 corresponds to a computing system or device of the medical imaging system 104. The computing device 200 includes a computing unit 202 and a memory 204. The computing unit 202 may be implemented as one or more microprocessors, microcomputers, microcontrollers, digital signal processors, central processing units, graphical processing units, state machines, logic circuitries, and/or any devices that manipulate signals based on operational instructions. Among other capabilities, the computing unit 202 may be configured to fetch and execute computer-readable instructions stored in the memory 204. In an aspect of the present disclosure, the memory 204 may include any computer-readable medium known in the art including, for example, volatile memory, such as static random access memory (SRAM) and dynamic random access memory (DRAM) and/or nonvolatile memory, such as read only memory (ROM), erasable programmable ROM, flash memories, hard disks, optical disks, and magnetic tapes. The memory 204 may be capable of storing data and allowing any storage location to be directly accessed by the computing unit 202.

Aspects of the present disclosure relate to a method for processing ultrasound images of region around the SSP tendon to generate 3D visualization of the SSP tendon. The present disclosure pertains to an improved method for segmentation and 3D reconstruction of ultrasound images which results in better focused images, improved clarity, and automated diagnosis of disorders (or injuries) related to the SSP tendon. It is often desirable in medical imaging to segment a portion of the image displayed in the image plane for selective processing. Ultrasound images are grayscale images used for the diagnosis of various pathological conditions (or disorders). The ultrasound images have low resolution and contrast, resulting in a higher dependency on the physician, technician, or radiologist operating the ultrasound imaging device to analyze the ultrasound images. Aspects of the present disclosure are directed to interactive visualization of SSP tendon injury in ultrasound images through segmentation and 3D reconstruction, thus automating the diagnostics performed from the ultrasound images to make the process more reliable and less dependent on the physician, technician, or radiologist.

According to aspects of the present disclosure, the computing device 200 may also include a data acquisition module 206, a segmentation module 208, a 3D reconstruction module 210, a rendering module 212, and a data storage 214.

The data acquisition module 206 may acquire the plurality of ultrasound images generated by the ultrasound imaging device 102. In an aspect of the present disclosure, the plurality of ultrasound images may correspond to the region of the patient's body around the SSP tendon. The data acquisition module 206 may receive the plurality of ultrasound images directly from the ultrasound imaging device 102 in real-time, i.e., when the high frequency ultrasound probe is pressed against the skin of the patient to generate the plurality of ultrasound images. The data acquisition module 206 may also receive the plurality of ultrasound images stored or archived in the storage device 106. The data acquisition module 206 may receive the plurality of ultrasound images over the network 110.

The segmentation module 208 performs one or more image processing techniques or algorithms on the plurality of ultrasound images to perform image segmentation. The image segmentation refers to a process of dividing an image into different regions based on characteristics of pixels to identify objects or boundaries to simplify and efficiently analyze the image.

The segmentation module 208 preprocesses the plurality of ultrasound images. The plurality of ultrasound images may have poor resolution and contrast which may cause image segmentation algorithms to poorly segment a region of interest from the plurality of ultrasound images. The segmentation module 208 preprocesses the plurality of ultrasound images by applying statistically adaptive contrast enhancement to the plurality of ultrasound images followed by speckle removal.

In an aspect of the present disclosure, considering that speckle in an ultrasound image follows Rayleigh pattern, the segmentation module 208 may enhance contrast of the plurality of ultrasound images using a Rayleigh distribution. The probability and cumulative density function (CDF) of Rayleigh distribution may be used to map contrast enhanced pixels to an image grid. Image pixels may be mapped to a plurality of contrast enhanced ultrasound images using CDF of the Rayleigh distribution. Contrast enhancement of the plurality of ultrasound images makes the boundaries and speckle in the plurality of ultrasound images more prominent. To keep the boundaries prominent, the segmentation module 208 may perform removal of speckle from homogeneous regions of the plurality of contrast enhanced ultrasound images using an anisotropic diffusion method. Contrast enhancement and speckle removal from the plurality of ultrasound images result in a plurality of preprocessed ultrasound images composed of pixels.

Further, the segmentation module 208 minimizes an energy of the plurality of preprocessed ultrasound images to generate a plurality of low energy preprocessed ultrasound images. In an aspect of the present disclosure, the segmentation module 208 may apply an evolutionary algorithm, such as the Darwinian Particle Swarm Optimization (DPSO) algorithm to minimize the energy of the plurality of preprocessed ultrasound images.

Further, the segmentation module 208 extracts a set of SSP tendon images from the plurality of low energy preprocessed ultrasound images. In an aspect of the present disclosure, the segmentation module 208 may apply an image segmentation algorithm, such as the enhanced Chan-Vese algorithm, to extract the set of SSP tendon images from the plurality of low energy preprocessed ultrasound images.

Further, the segmentation module 208 performs a morphological operation on the set of SSP tendon images. In an aspect of the present disclosure, morphological operations refer to a set of image processing operations that process images based on shapes. The morphological operations apply a structuring element to an input image to create an output image of the same size. In a morphological operation, the value of each pixel in the output image is based on a comparison of the corresponding pixel in the input image with its neighbors. Dilation and erosion are the most basic morphological operations. Dilation operation adds pixels to the boundaries of objects in an image, and erosion operation removes pixels on object boundaries. The dilation and erosion operations may be used in combination to implement various image processing operations, such as morphological opening operation and morphological closing operation. The morphological opening operation erodes an image and then dilates the eroded image, using the same structuring element for both operations. The morphological opening operation removes small objects from an image while preserving the shape and size of larger objects in the image. The morphological closing operation dilates an image and then erodes the dilated image, using the same structuring element for both operations. The morphological closing operation fills small holes from an image while preserving the shape and size of the objects in the image. The dilation operation and the erosion operation may be combined to remove small objects from the image and smooth the border of large objects in the image. The segmentation module 208 may perform one or more morphological operations on the set of SSP tendon images to generate a smoothed set of SSP tendon images.

Further, the segmentation module 208 applies a binary mask to the smoothed set of SSP tendon images to detect boundary points of the SSP tendon. A set of segmented image frames are generated as a result of applying the binary mask to the smoothed set of SSP tendon images. The segmentation module 208 may apply the binary mask by setting the pixels in the smoothed set of SSP tendon images to zero when a corresponding pixel in the binary mask is zero. The segmentation module 208 may detect the boundary points by comparing each remaining pixel to an edge point of the binary mask. The segmentation module 208 stores the set of segmented image frames in the data storage 214.

The 3D reconstruction module 210 obtains the set of segmented image frames from the data storage 214. The 3D reconstruction module 210 arranges the set of segmented image frames based on a spatial position of each segmented image frame with respect to the SSP tendon. The 3D reconstruction module 210 may apply an image registration process to arrange the set of segmented image frames based on the spatial position. The image registration refers to a process of overlaying or aligning two or more images (i.e., the set of segmented image frames of the present disclosure) of a same scene or object. The two or more images may be taken at different times, from different viewpoints, and/or by different imaging sensors. One of the two or more images may be designated as a reference image in the image registration process. The image registration process superimposes pixels from the reference image to the other (or target) image(s) by aligning the two or more images into a common coordinate system. The two or more images may be aligned using the image registration process into a single composition to represent the scene or object in 3D.

The 3D reconstruction module 210 reconstructs a 3D representation of the SSP tendon. To reconstruct the 3D representation of the SSP tendon the 3D reconstruction module 210 applies an enhanced marching cubes operation on the arranged set of segmented image frames. The enhanced marching cubes operation eliminates uncertainties in contrast variations, removes duplicate vertices, and smooths surface and boundaries. Applying the enhanced marching cubes operation on the arranged set of segmented image frames results in generating an enhanced set of segmented image frames. The 3D reconstruction module 210 forms a 3D mesh of the enhanced set of segmented images.

In an aspect of the present disclosure, the enhanced marching cubes operation includes a 3D smoothing operation, a 3D median filtering operation, and a marching cubes algorithm.

The 3D smoothing operation refers to removal or reducing of noise while preserving important features. 3D smoothing may produce a less pixelated image. In some examples, the smoothing operation may be based on low-pass filtering. In some other examples, the smoothing operations may be based on calculating an average or median value of a group of pixels that moves through the image.

The 3D median filtering operation refers to a windowed filter of a nonlinear class which is used for image quality improvement. The 3D median filtering operation is widely used in digital image processing as it preserves edges while removing noise from the image. The 3D median filtering operation considers each pixel in the image and looks at its nearby neighbors to decide whether or not it is representative of its surroundings. The 3D median filtering operation replaces a pixel value with the median of neighboring pixel values. The median is calculated by first sorting all the pixel values from the neighboring pixels into numerical order and then replacing the pixel value of the pixel being considered with the middle pixel value. If the neighboring pixels under consideration contain an even number of pixels, the average of the two middle pixel values is used. The 3D median filtering operation is useful to eliminate speckle noise in medical imaging applications such as ultrasonic medical imaging.

The marching cubes operation or marching cubes algorithm refers to a computer graphics algorithm for extracting a polygonal mesh of an iso-surface from a 3D discrete scalar field (the elements of which are also referred to as voxels). The application of the marching cubes algorithm is used with 3D visualization of medical images. The marching cubes algorithm proceeds through the scalar field, taking eight neighbor locations at a time to form an imaginary cube, and then determining a polygon(s) needed to represent the part of the iso-surface that passes through this cube. The individual polygons are then fused into the desired surface. The marching cubes algorithm creates an index to a precalculated array of 256 possible polygon configurations ($2^8=256$) within the cube, by treating each of the 8 scalar values as a bit in an 8-bit integer. If the scalar value is higher than the iso-value (i.e., it is inside the surface) then the appropriate bit is set to one, while if the scalar's value is lower than the iso-value (i.e., it is outside the surface), the appropriate bit is set to zero. The final value, after all eight scalars are checked, is the actual index to the polygon indices array. Finally, each vertex of the generated polygons is placed on the appropriate position along the cube's edge by linearly interpolating the two scalar values that are connected by that edge. The gradient of the scalar field at each grid point is also the normal vector of a hypothetical iso surface passing from that point. Therefore, each normal vector may be interpolated along the edges of each cube to find the normal of the generated vertices which are essential for shading the resulting mesh with an illumination model.

Further, the 3D reconstruction module 210 performs a patching operation on the 3D mesh to form a patched 3D mesh. Performing the patching operation increases the density of the 3D mesh. The patching operation may be performed by filling in open areas of the 3D mesh with pixels having an intensity equal to that of a neighboring pixel. Further, the 3D reconstruction module 210 smooths the patched 3D mesh by z-buffer rendering to generate the 3D representation of the SSP tendon.

The 3D reconstruction module 210 may store the 3D representation of the SSP tendon in the data storage 214 or transmit the 3D representation of the SSP tendon to the storage device 106 for archival (or storage).

The rendering module 212 may render the 3D representation of the SSP tendon on the display devices 108. In an aspect of the present disclosure, a user, such as a doctor, a radiologist, or any other user may access the computing device 200 via the display device 108 to display the 3D representation of the SSP tendon on the display device 108. The rendering module 212 may retrieve the 3D representation of the SSP tendon from the data storage 214 or the storage device 106 and render the 3D representation of the SSP tendon on the display device 108.

The data storage 214 may store the plurality of ultrasound images acquired by the data acquisition module, the smoothed set of SSP tendon images and the set of segmented image frames generated by the segmentation module 208, and the 3D representation of the SSP tendon generated by the 3D reconstruction module 210. The data storage 214 may store one or more of final data and any intermediate data generated as a result of processing the plurality of ultrasound images.

According to some aspects of the present disclosure, the data acquisition module 206, the segmentation module 208, the 3D reconstruction module 210, and the rendering module 212, amongst other modules, may include routines, programs, objects, components, and data structures which may perform particular tasks or implement particular abstract data types. The data acquisition module 206, the segmentation module 208, the 3D reconstruction module 210, and the rendering module 212, may also be implemented as, signal processor(s), state machine(s), logic circuitries, and/or any other device or component that manipulate signals based on operational instructions.

According to some aspects of the present disclosure, the data acquisition module 206, the segmentation module 208, the 3D reconstruction module 210, and the rendering module 212 may be implemented in hardware, instructions executed by a processing unit, or by a combination thereof. The processing unit may comprise a computer, a processor, a state machine, a logic array, or any other suitable devices capable of processing instructions. The processing unit may be a general-purpose processor which executes instructions to cause the general-purpose processor to perform the required tasks or, the processing unit may be dedicated to perform the required functions. In some embodiments, the data acquisition module 206, the segmentation module 208, the 3D reconstruction module 210, and the rendering module 212 may be machine-readable instructions which, when executed by a processor/processing unit, perform any of desired functionalities. The machine-readable instructions may be stored on an electronic memory device, hard disk, optical disk or other machine-readable storage medium or non-transitory medium. In an implementation, the machine-readable instructions may also be downloaded to the storage medium via a network connection. In an example, machine-readable instructions may be stored in the computing unit 202.

In an aspect of the present disclosure, the computing device 200 may receive the plurality of ultrasound images generated by the ultrasound imaging device 102 in real-time. The computing device 200 may process the plurality of ultrasound images in real-time to generate the 3D representation of the SSP tendon. In another aspect of the present disclosure, a plurality of ultrasound images may have been generated and stored in the storage device 106 in the past. The computing device 200 may retrieve and process the stored plurality of ultrasound images to generate 3D representation of the SSP tendon.

In an aspect of the present disclosure, one or more functionalities of the computing device 200 may be hosted on a server computing device or a cloud computing environment.

In an aspect of the present disclosure, the data acquisition module 206, the segmentation module 208, the 3D reconstruction module 210, and the rendering module 212 may collectively correspond to a medical imaging software or a computer application that may be installed in the computing device 200. The computing device 200 acts as a central computing device to execute the medical imaging software or computer application to perform the image processing methods on the plurality of ultrasound images, and the final output of the image processing method is displayed on the display device 108 or on a display of the ultrasound imaging device 102.

In an aspect of the present disclosure, the medical imaging software or computer application may be installed in and executed by one or more of the ultrasound imaging device 102, the medical imaging system 104 (or the computing device 200), and the display devices 108.

Figure 3:
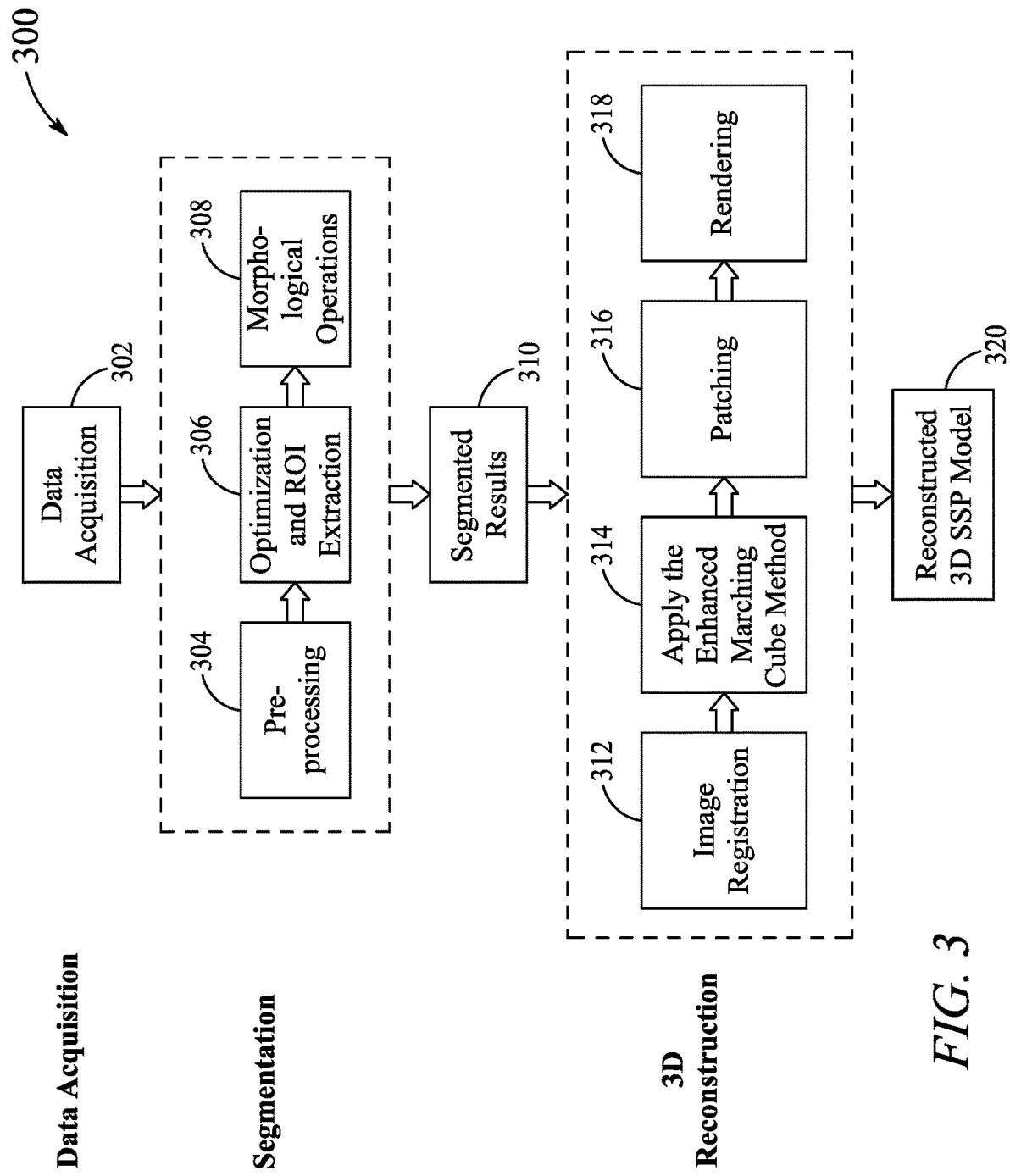
FIG. 3 is a process flow diagram for reconstructing 3D visualization of ultrasound images of supraspinatus (SSP) tendon, according to certain embodiments.

FIG. 3 depicts a process flow diagram 300 for reconstructing 3D visualization of ultrasound images of the SSP tendon, according to exemplary aspects of the present disclosure.

As explained with reference to FIG. 2, the plurality of ultrasound images are reconstructed to generate the 3D representation of the SSP tendon. According to aspects of the present disclosure, generating the 3D representation of the SSP tendon includes three image processing stages, 1) a data acquisition stage, 2) a segmentation stage, and 3) a 3D reconstruction stage. Functionalities of the three image processing stages, the data acquisition stage, the segmentation stage, and the 3D reconstruction stage are explained in detail with reference to the data acquisition module 206, the segmentation module 208, and the 3D reconstruction module 210, respectively, of FIG. 2.

The functionalities of the first stage, i.e., the data acquisition stage, includes data acquisition 302. The functionalities of the second stage, i.e., the segmentation stage includes pre-processing 304, optimization and region of interest (ROI) extraction 306, and morphological operations 308. Segmented results 310 are generated as a result of the segmentation stage. The functionalities of the third stage, i.e., the 3D reconstruction stage includes image registration 312, applying the enhanced marching cubes method 314, patching 316, and rendering 318. The 3D representation of the SSP tendon 320 is reconstructed as a result of the 3D reconstruction stage.

At process block 302, the plurality of ultrasound images are acquired. At process block 304, the plurality of ultrasound images are preprocessed by applying statistically adaptive contrast enhancement and speckle removal. At process block 306, optimization and ROI extraction is performed on the plurality of preprocessed ultrasound images. The plurality of low energy preprocessed ultrasound images are generated by minimizing energy of the plurality of preprocessed ultrasound images. The energy of the plurality of preprocessed ultrasound images is minimized by applying the evolutionary algorithm, such as the Darwinian particle swarm optimization algorithm. The set of SSP tendon images are extracted from the plurality of low energy preprocessed ultrasound images by applying the segmentation algorithm, such as the enhanced Chan-Vese algorithm. At process block 308, morphological operations are performed on the set of SSP tendon images to generate the smoothed set of SSP tendon images. The binary mask is applied by setting the pixels in the smoothed set of SSP tendon images to zero when a corresponding pixel in the binary mask is zero, and the boundary points are detected for the SSP tendon. At process block 310, the segmented results, i.e., the set of segmented image frames is generated.

An enhanced Chan-Vese algorithm is a classical active contour model designed to segment objects without clearly defined boundaries. This algorithm is based on level sets that are evolved iteratively to minimize an energy, which is defined by weighted values corresponding to the sum of differences intensity from the average value outside the segmented region, the sum of differences from the average value inside the segmented region, and a term which is dependent on the length of the boundary of the segmented region. (See: Chan, T; Vese, L., "An Active Contour Model Without Edges", Scale-Space Theories in Computer Vision, 1999, DOI:10.1007/3-540-48236-9_13, incorporated herein by reference in its entirety).

At process block 312, the set of segmented image frames are arranged based on the spatial position by applying the image registration. At process block 314, the enhanced marching cubes operation is applied on the adjusted set of segmented image frames to eliminate uncertain contrast variation, remove duplicate vertices, and smooth surface and boundaries. Applying the enhanced marching cubes operation generates the enhanced set of segmented image frames. At process block 316, the patched 3D mesh of the enhanced set of segmented images is formed. At process block 318, the patched 3D mesh is smoothed by the z-buffer rendering to generate a 3D model of the SSP tendon. At block 320, the 3D representation of the SSP tendon is reconstructed.

The segmentation stage may use various image processing algorithms, such as Adaptive Histogram Equalization (AHE), DPSO, and Chan-Vese. However, even after applying the DPSO and Chan-Vese algorithms, the obtained results may not be significant enough to visually interpret the SSP tendon. The segmentation stage requires morphological operations to be performed for smooth and accurate boundaries of the SSP tendon, resulting in the extraction of a single and accurate object (or region) as the SSP tendon in resultant images. Further, in the 3D reconstruction stage, the enhanced marching cubes algorithm is applied to slices of the extracted SSP tendon region in the resultant images for 3D reconstruction of the SSP tendon.

The 3D reconstruction has a better 3D outcome with adequate smoothing. This reduces the number of duplicate vertices, reduces undesirable shining, and eliminates undesired and detached elements from the 3D representation. The obtained outcome is significantly smoothed and accurate, resulting in precise interpretation capability to diagnose the disorders.

Performance Evaluation Metrics

According to aspects of the present disclosure, several metrics can be used to analyze the performance of segmentation and 3D Reconstruction.

Performance Metrics for Segmentation

1) Sensitivity: Sensitivity may be defined as the proportion of true positives that are correctly identified by a diagnostic test.

2) Specificity: Specificity may be defined as the proportion of true negatives correctly identified by the diagnostic test. Specificity suggests how well the diagnostic test identifies the normal (negative) condition.

3) Accuracy: Accuracy may be defined as the proportion of true results, either true positive or true negative, in a population. Accuracy measures the degree of accuracy of the diagnostic test on a condition.

4) Segmented Area: The extracted desired and meaningful region from an input image is referred to as a segmented area. The segmented area is determined by calculating the number of pixels in the extracted region.

5) Area Ratio: The area ratio of the segmented area is estimated by the ratio of the segmented area and the original area of the image.

Performance Metrics for the 3D Reconstruction

1) Volume calculation: The volume is determined as the total number of voxels in the reconstructed 3D model multiplied with a voxel size. Minkowski measures also use a similar method to calculate the volume.

2) Thickness calculation: Minkowski measurement is also used in the calculation of the thickness of the reconstructed 3D model.
3) Roughness calculation: Surface roughness is a component of surface texture.

According to aspects of the present disclosure, the segmentation and 3D reconstruction of ultrasound images have several advantages. The segmentation of ultrasound images enables accurate and optimized segmentation of the SSP tendon from 2D ultrasound images. The 3D reconstruction of ultrasound images generates accurate and efficient 3D models having a) a surface smoother than in the conventional iso-surface method, b) extra shining removed from the output image that helps in the accurate analysis of the image, c) the disconnected parts of the image removed with no beneficial information removed (such as removed duplicate vertices), and d) small spots removed from the image surface. Further, the segmentation and 3D reconstruction disclosed by the present disclosure facilitates better visualization of disorders related to SSP tendon.

Figure 4:
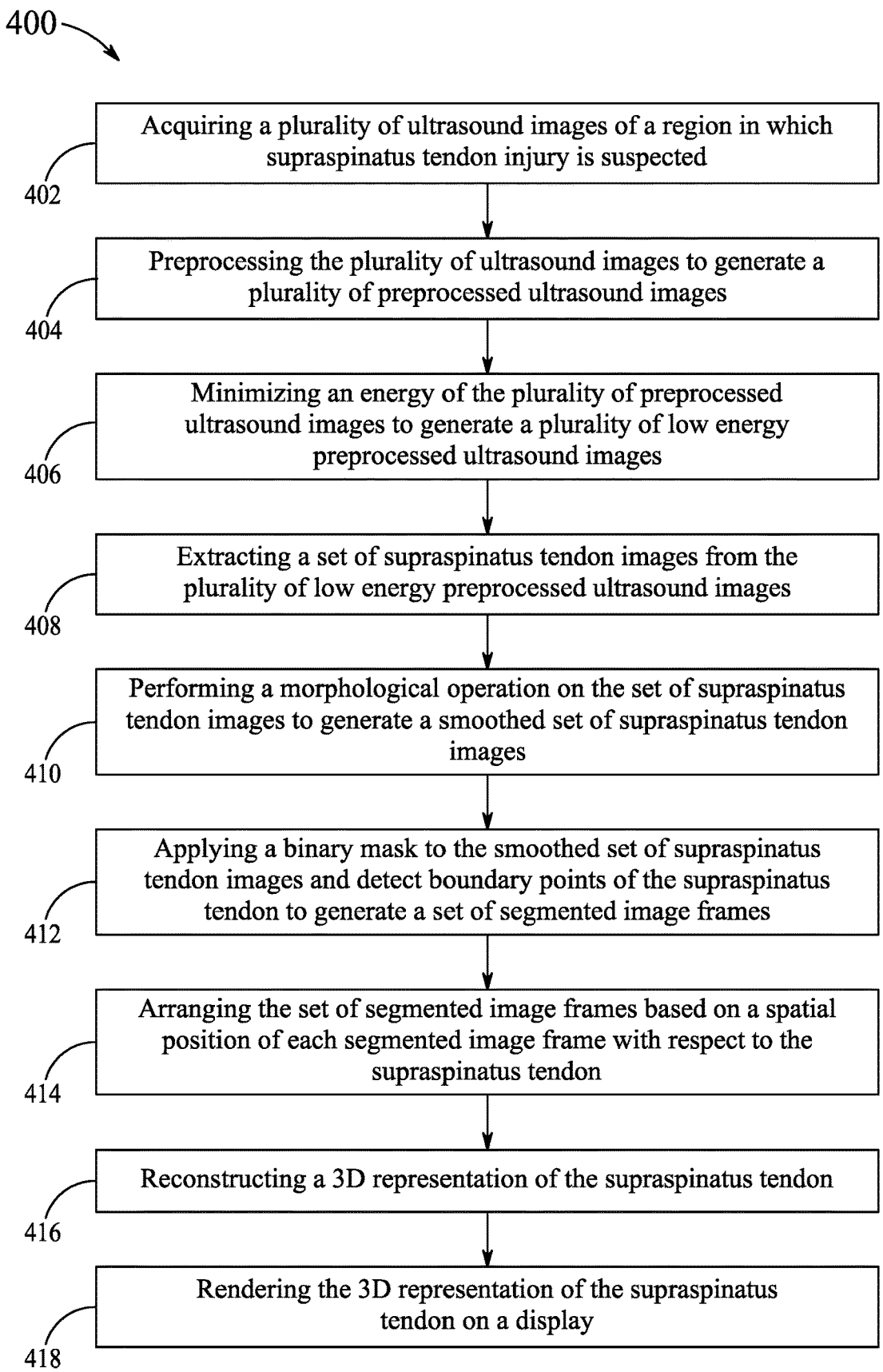
FIG. 4 is an exemplary flowchart of interactive 3D visualization of ultrasound images of a supraspinatus tendon injury, according to certain embodiments.

FIG. 4 depicts an exemplary flowchart 400 of interactive 3D visualization of ultrasound images of a SSP tendon injury, according to exemplary aspects of the present disclosure.

At step 402, the method includes acquiring a plurality of ultrasound images of a region in which the SSP tendon injury is suspected.

At step 404, the method includes preprocessing the plurality of ultrasound images. The plurality of ultrasound images are preprocessed to generate a plurality of preprocessed ultrasound images composed of pixels.

At step 406, the method includes minimizing an energy of the plurality of preprocessed ultrasound images to generate a plurality of low energy preprocessed ultrasound images.

At step 408, the method includes extracting a set of SSP tendon images from the plurality of low energy preprocessed ultrasound images.

At step 410, the method includes performing a morphological operation on the set of SSP tendon images to generate a smoothed set of SSP tendon images.

At step 412, the method includes applying a binary mask to the smoothed set of SSP tendon images to detect boundary points of the SSP tendon. As a result, a set of segmented image frames is generated.

At step 414, the method includes arranging the set of segmented image frames based on a spatial position of each segmented image frame with respect to the SSP tendon.

At step 416, the method includes reconstructing a 3D representation of the SSP tendon.

At step 418, the method includes rendering the 3D representation of the supraspinatus tendon on the display device(s) 108.

Figure 5:
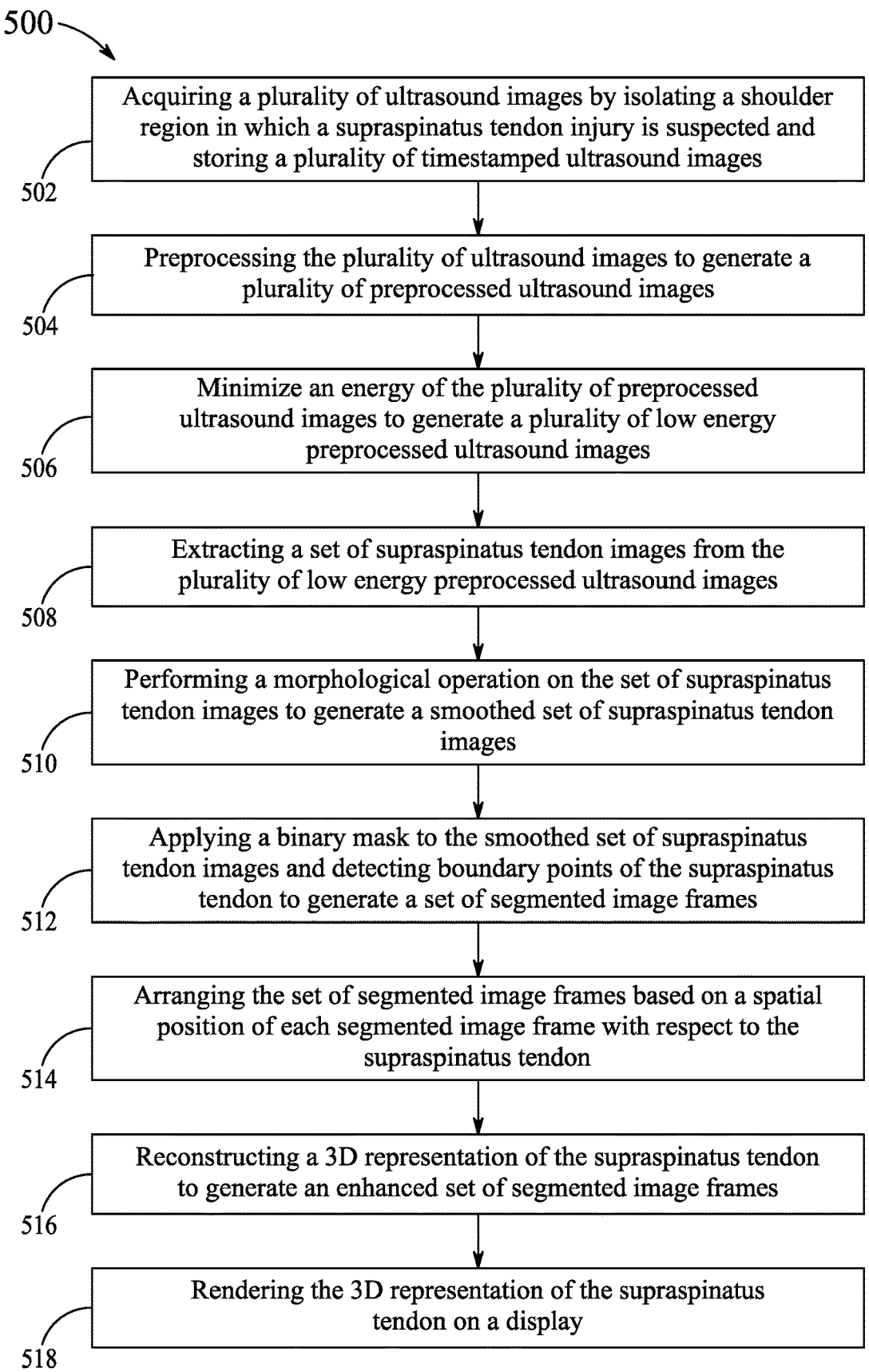
FIG. 5 is another exemplary flowchart of interactive 3D visualization of ultrasound images of a supraspinatus tendon injury, according to certain embodiments.

FIG. 5 depicts another exemplary flowchart 500 of interactive 3D visualization of ultrasound images of a SSP tendon injury, according to exemplary aspects of the present disclosure.

At step 502, the method includes acquiring a plurality of ultrasound images of a region in which the SSP tendon injury is suspected. A shoulder region in which the SSP tendon injury is suspected is isolated and the shoulder region is imaged by a high frequency ultrasound probe. A plurality of timestamped ultrasound images composed of pixels are stored in a database.

At step 504, the method includes preprocessing the plurality of ultrasound images by applying statistically adaptive contrast enhancement and speckle removal to generate a plurality of preprocessed ultrasound images.

At step 506, the method includes minimizing an energy of the plurality of preprocessed ultrasound images by applying an evolutionary algorithm. The evolutionary algorithm is a Darwinian particle swarm optimization. A plurality of low energy preprocessed ultrasound images are generated as a result of applying the evolutionary algorithm.

At step 508, the method includes extracting a set of SSP tendon images from the plurality of low energy preprocessed ultrasound images by applying a segmentation algorithm. The segmentation algorithm is an enhanced Chan-Vese algorithm.

At step 510, the method includes performing a morphological operation on the set of SSP tendon images to generate a smoothed set of SSP tendon images.

At step 512, the method includes applying a binary mask to the smoothed set of SSP tendon images to detect boundary points of the SSP tendon. The binary mask is applied by setting the pixels in the smoothed set of SSP tendon images to zero when a corresponding pixel in the binary mask is zero. The boundary points are detected by comparing each remaining pixel to an edge point of the binary mask. A set of segmented image frames are generated as a result of applying the binary mask.

At step 514, the method includes arranging the set of segmented image frames based on a spatial position of each segmented image frame with respect to the SSP tendon by image registration.

At step 516, the method includes reconstructing a 3D representation of the SSP tendon by applying an enhanced marching cubes operation on the set of segmented image frames to remove duplicate vertices and smooth surfaces and boundaries. An enhanced set of segmented image frames are generated as a result of applying the enhanced marching cubes operation. A 3D mesh of the enhanced set of segmented image frames is formed. A patched 3D mesh is formed by filling in open areas of the 3D mesh with pixels having an intensity equal to that of a neighboring pixel.

At step 518, the method includes rendering the 3D representation of the SSP tendon on the display device(s) 108.

The first embodiment is illustrated with respect to FIGS. 1-8. The first embodiment describes a system for interactive 3D visualization of ultrasound images of a supraspinatus tendon injury. The system comprises a high frequency ultrasound probe configured to image a region in which the supraspinatus tendon injury is suspected, and generate a plurality of ultrasound images composed of pixels; a database configured to store the plurality of ultrasound images; a display device 108; a computing device 200 operatively connected to the database and the display device 108, the computing device 200 including circuitry and a non-transitory computer readable medium having instructions stored therein. The instructions are executed by one or more processors to acquire the plurality of ultrasound images from the database; preprocess the plurality of ultrasound images to generate a plurality of preprocessed ultrasound images; minimize an energy of the plurality of preprocessed ultrasound images to generate a plurality of low energy preprocessed ultrasound images; extract, from the plurality of low energy preprocessed ultrasound images, a set of supraspinatus tendon images; perform a morphological operation on the set of supraspinatus tendon images to generate a smoothed set of supraspinatus tendon images; apply a binary mask to the smoothed set of supraspinatus tendon images to detect boundary points of the supraspinatus tendon to generate a set of segmented image frames; arrange the set of segmented image frames based on a spatial position of each segmented image frame with respect to the supraspinatus tendon; reconstruct a 3D representation of the supraspinatus tendon; and render the 3D representation of the supraspinatus tendon on the display device(s) 108.

The computing device 200 is configured to preprocess the plurality of ultrasound images by applying statistically adaptive contrast enhancement and speckle removal.

The computing device 200 is configured to minimize the energy of each of the plurality of preprocessed ultrasound images by applying an evolutionary algorithm.

The evolutionary algorithm is a Darwinian particle swarm optimization.

The computing device 200 is configured to extract the set of supraspinatus tendon images by applying a segmentation algorithm.

The segmentation algorithm is an enhanced Chan-Vese algorithm.

The computing device 200 is configured to apply the binary mask by setting the pixels in the smoothed set of supraspinatus tendon images to zero when a corresponding pixel in the binary mask is zero; and detect the boundary points by comparing each remaining pixel to an edge point of the binary mask.

The computing device 200 is configured to apply an enhanced marching cubes operation on the set of segmented image frames to remove duplicate vertices and smooth surface and boundaries to generate an enhanced set of segmented image frames; form a 3D mesh of the enhanced set of segmented image frames; form a patched 3D mesh by filling in open areas of the 3D mesh with pixels having an intensity equal to that of a neighboring pixel; and smooth the patched 3D mesh by z-buffer rendering to generate a reconstruction of the 3D representation of the supraspinatus tendon.

The second embodiment is illustrated with respect to FIGS. 1-8. The second embodiment describes a method for interactive 3D visualization of ultrasound images of a supraspinatus tendon injury. The method comprising acquiring a plurality of ultrasound images of a region in which the supraspinatus tendon injury is suspected; preprocessing the plurality of ultrasound images, thus generating a plurality of preprocessed ultrasound images composed of pixels; minimizing an energy of the plurality of preprocessed ultrasound images, thus generating a plurality of low energy preprocessed ultrasound images; extracting, from the plurality of low energy preprocessed ultrasound images, a set of supraspinatus tendon images; performing a morphological operation on the set of supraspinatus tendon images, thus generating a smoothed set of supraspinatus tendon images; applying a binary mask to the smoothed set of supraspinatus tendon images to detect boundary points of the supraspinatus tendon, thus generating a set of segmented image frames; arranging the set of segmented image frames based on a spatial position of each segmented image frame with respect to the supraspinatus tendon; reconstructing a 3D representation of the supraspinatus tendon; and rendering the 3D representation of the supraspinatus tendon on the display device(s) 108.

The method further comprising acquiring the plurality of ultrasound images by: isolating a shoulder region in which the supraspinatus tendon injury is suspected; imaging the shoulder region by a high frequency ultrasound probe and generating a plurality of timestamped ultrasound images; storing the plurality of timestamped ultrasound images in a database; and retrieving a time series of the plurality of timestamped ultrasound images from the database.

The method further comprising preprocessing the plurality of ultrasound images by applying statistically adaptive contrast enhancement and speckle removal.

The method further comprising minimizing the energy of each of the plurality of preprocessed ultrasound images by applying an evolutionary algorithm.

The evolutionary algorithm is a Darwinian particle swarm optimization.

The method further comprising extracting the set of supraspinatus tendon images by applying a segmentation algorithm.

The segmentation algorithm is an enhanced Chan-Vese algorithm.

The method further comprising applying the binary mask by setting the pixels in the smoothed set of supraspinatus tendon images to zero when a corresponding pixel in the binary mask is zero; and detecting the boundary points by comparing each remaining pixel to an edge point of the binary mask.

The method further comprising arranging the set of segmented image frames based on the spatial position by image registration.

The method further comprising reconstructing the 3D representation of the supraspinatus tendon by: applying an enhanced marching cubes operation on the set of segmented image frames to remove duplicate vertices and smooth surface and boundaries, thus generating an enhanced set of segmented image frames; forming a 3D mesh of the enhanced set of segmented image frames; and forming a patched 3D mesh by filling in open areas of the 3D mesh with pixels having an intensity equal to that of a neighboring pixel.

The method further comprising smoothing the patched 3D mesh by z-buffer rendering.

The third embodiment is illustrated with respect to FIGS. 1-8. The third embodiment describes a method for interactive 3D visualization of ultrasound images of a supraspinatus tendon injury. The method comprising acquiring a plurality of ultrasound images of a region in which the supraspinatus tendon injury is suspected by isolating a shoulder region in which the supraspinatus tendon injury is suspected, imaging the shoulder region by a high frequency ultrasound probe and storing a plurality of timestamped ultrasound images composed of pixels; preprocessing the plurality of ultrasound images by applying statistically adaptive contrast enhancement and speckle removal, thus generating a plurality of preprocessed ultrasound images; minimizing an energy of the plurality of preprocessed ultrasound images by applying an evolutionary algorithm, wherein the evolutionary algorithm is a Darwinian particle swarm optimization, thus generating a plurality of low energy preprocessed ultrasound images; extracting, from the plurality of low energy preprocessed ultrasound images, a set of supraspinatus tendon images by applying a segmentation algorithm, wherein the segmentation algorithm is an enhanced Chan-Vese algorithm; performing a morphological operation on the set of supraspinatus tendon images, thus generating a smoothed set of supraspinatus tendon images; applying a binary mask to the smoothed set of supraspinatus tendon images to detect boundary points of the supraspinatus tendon by setting the pixels in the smoothed set of supraspinatus tendon images to zero when a corresponding pixel in the binary mask is zero and detecting boundary points by comparing each remaining pixel to an edge point of the binary mask, thus generating a set of segmented image frames; arranging the set of segmented image frames based on a spatial position of each segmented image frame with respect to the supraspinatus tendon by image registration; reconstructing a 3D representation of the supraspinatus tendon by applying an enhanced marching cubes operation on the set of segmented image frames to remove duplicate vertices and smooth surface and boundaries, thus generating an enhanced set of segmented image frames, forming a 3D mesh of the enhanced set of segmented image frames, forming a patched 3D mesh by filling in open areas of the 3D mesh with pixels having an intensity equal to that of a neighboring pixel; and rendering the 3D representation of the supraspinatus tendon on the display device(s) 108.

Figure 6:
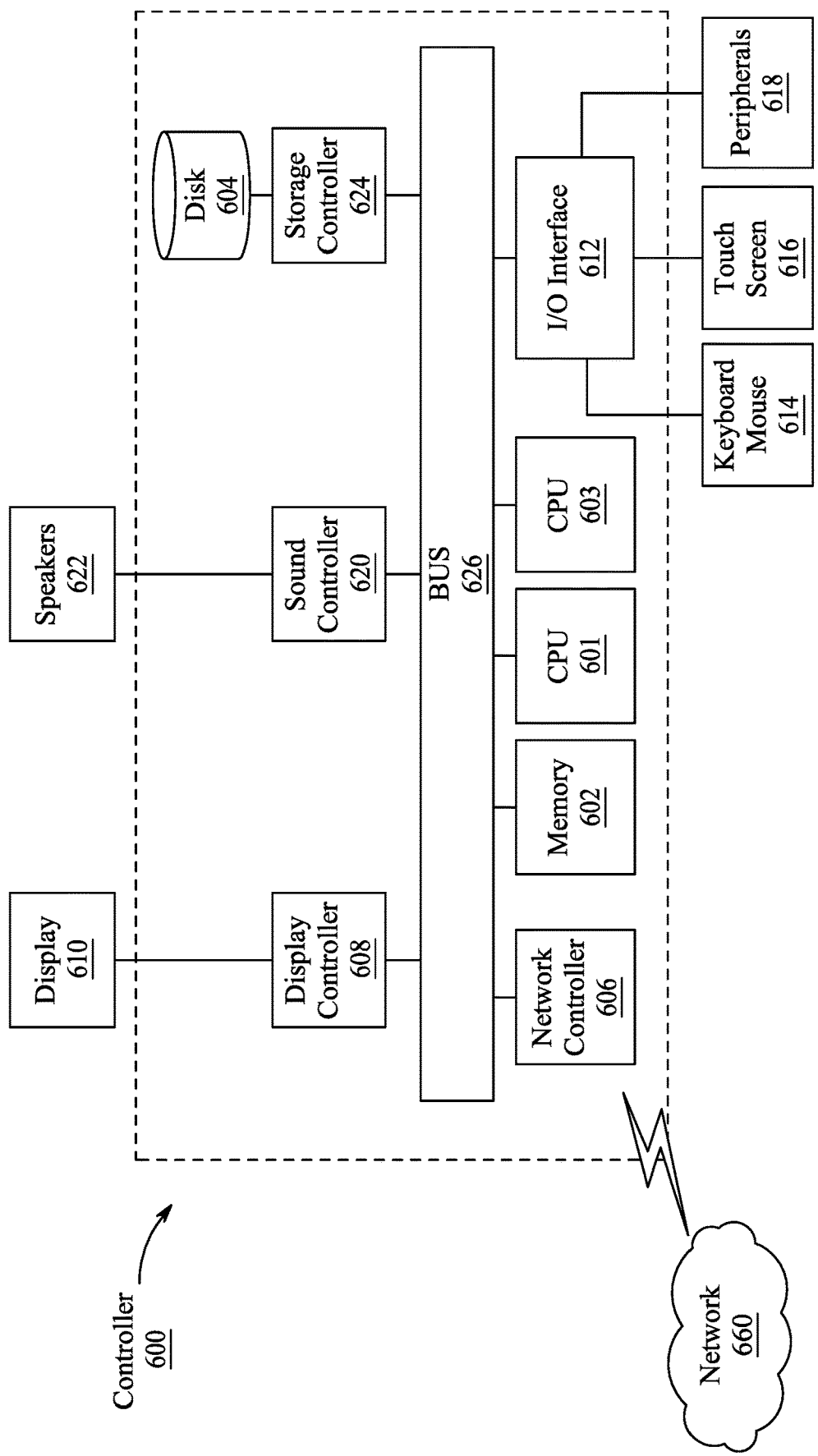
FIG. 6 is an illustration of a non-limiting example of details of computing hardware used in the computing device, according to certain embodiments.

FIG. 6 is an illustration of a non-limiting example of details of computing hardware used in the computing system associated with one or more of the ultrasound imaging device 102, the medical imaging system 104, the computing device 200, and the display device(s) 108, according to exemplary aspects of the present disclosure. In FIG. 6, a controller 600 is described in which the controller is a computing device which includes a CPU 601 which performs the processes described above/below. The process data and instructions may be stored in memory 602. These processes and instructions may also be stored on a storage medium disk 604 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 601, 603 and an operating system such as Microsoft Windows 7, Microsoft Windows 10, UNIX, Solaris, LINUX, Apple MAC-OS, and other systems known to those skilled in the art.

The hardware elements in order to achieve the computing device may be realized by various circuitry elements, known to those skilled in the art. For example, CPU 601 or CPU 603 may be a Xenon or Core processor from Intel of America or an Opteron processor from AMD of America, or may be other processor types that would be recognized by one of ordinary skill in the art. Alternatively, the CPU 601, 603 may be implemented on an FPGA, ASIC, PLD or using discrete logic circuits, as one of ordinary skill in the art would recognize. Further, CPU 601, 603 may be implemented as multiple processors cooperatively working in parallel to perform the instructions of the inventive processes described above.

The computing device in FIG. 6 also includes a network controller 606, such as an Intel Ethernet PRO network interface card from Intel Corporation of America, for interfacing with network 660. As can be appreciated, the network 660 can be a public network, such as the Internet, or a private network such as an LAN or WAN network, or any combination thereof and can also include PSTN or ISDN subnetworks. The network 660 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 608, such as a NVIDIA GeForce GTX or Quadro graphics adaptor from NVIDIA Corporation of America for interfacing with display 610, such as a Hewlett Packard HPL2445w LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners, such as an OfficeJet or DeskJet from Hewlett Packard.

A sound controller 620 is also provided in the computing device such as Sound Blaster X-Fi Titanium from Creative, to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the computing device. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 7.

Figure 7:
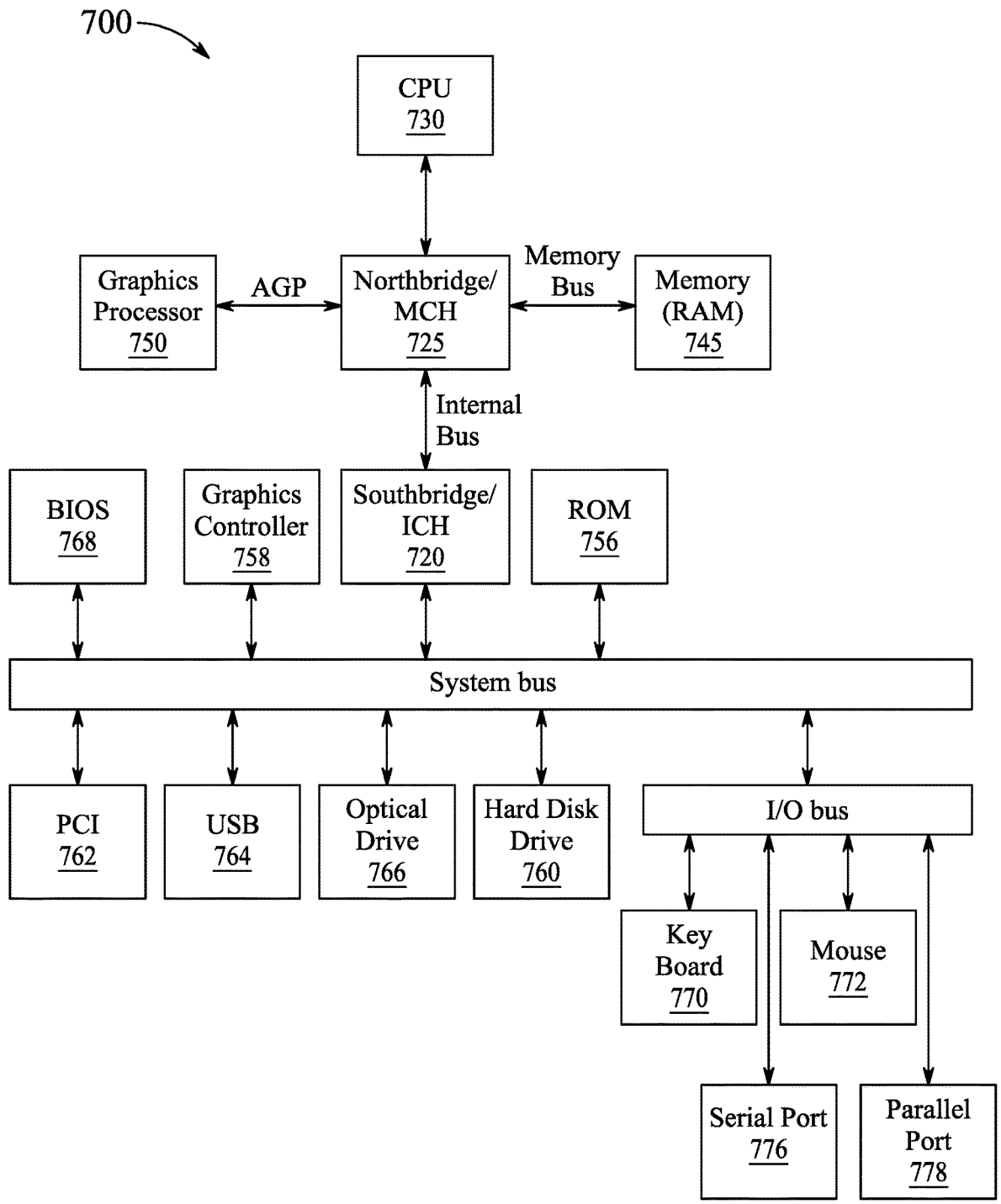
FIG. 7 is an exemplary schematic diagram of a data processing system used within the computing device, according to certain embodiments.

FIG. 7 shows a schematic diagram of a data processing system, according to certain embodiments, for performing the functions of the exemplary embodiments. The data processing system is an example of a computer in which code or instructions implementing the processes of the illustrative embodiments may be located.

In FIG. 7, data processing system 700 employs a hub architecture including a north bridge and memory controller hub (NB/MCH) 725 and a south bridge and input/output (I/O) controller hub (SB/ICH) 720. The central processing unit (CPU) 730 is connected to NB/MCH 725. The NB/MCH 725 also connects to the memory 745 via a memory bus, and connects to the graphics processor 750 via an accelerated graphics port (AGP). The NB/MCH 725 also connects to the SB/ICH 720 via an internal bus (e.g., a unified media interface or a direct media interface). The CPU Processing unit 730 may contain one or more processors and even may be implemented using one or more heterogeneous processor systems.

Figure 8:
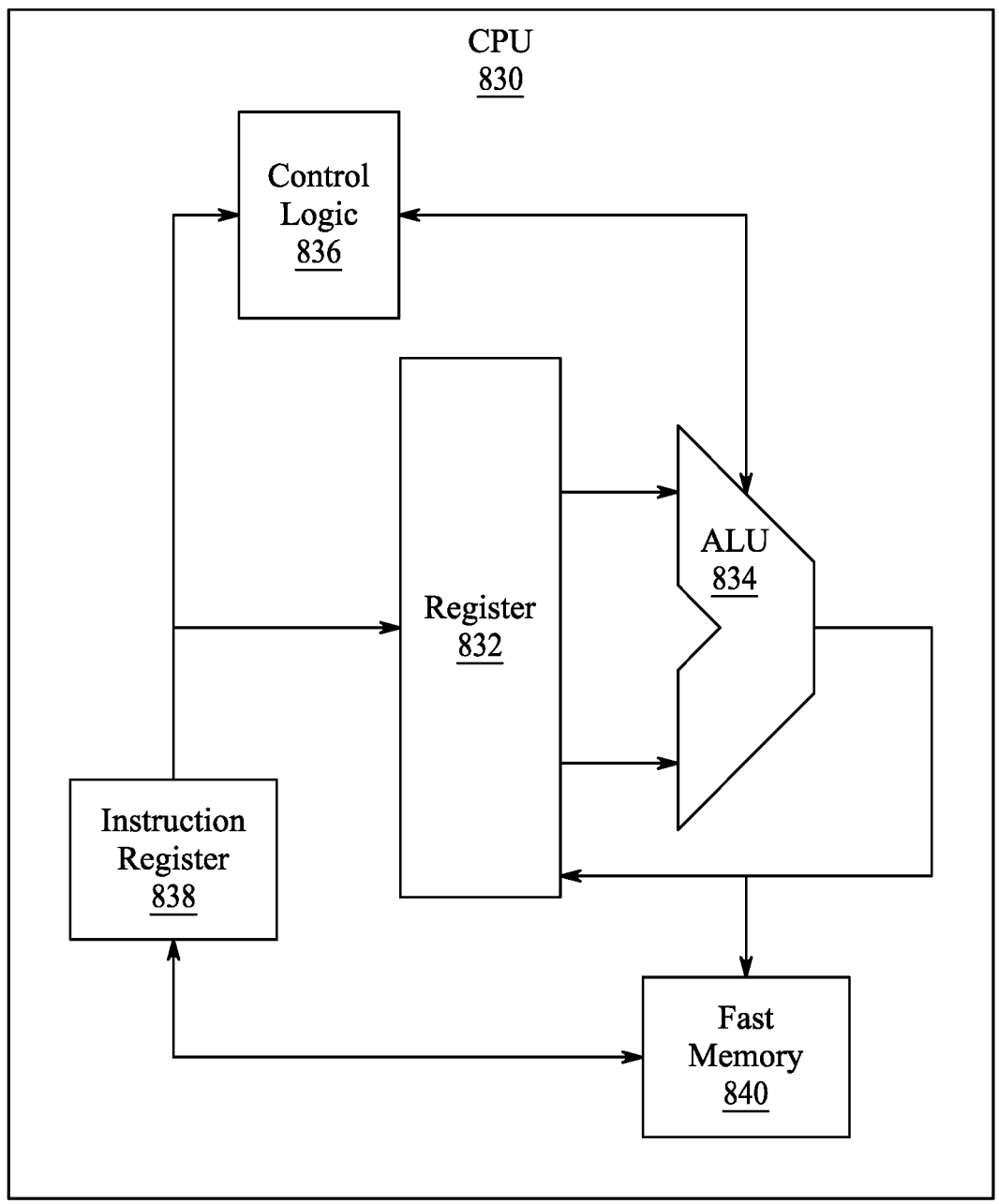
FIG. 8 is an exemplary schematic diagram of a processor used with the computing device, according to certain embodiments.

For example, FIG. 8 shows one implementation of CPU 730. In one implementation, the instruction register 838 retrieves instructions from the fast memory 840. At least part of these instructions are fetched from the instruction register 838 by the control logic 836 and interpreted according to the instruction set architecture of the CPU 730. Part of the instructions can also be directed to the register 832. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 834 that loads values from the register 832 and performs logical and mathematical operations on the loaded values according to the instructions. The results from these operations can be feedback into the register and/or stored in the fast memory 840. According to certain implementations, the instruction set architecture of the CPU 730 can use a reduced instruction set architecture, a complex instruction set architecture, a vector processor architecture, a very large instruction word architecture. Furthermore, the CPU 730 can be based on the Von Neuman model or the Harvard model. The CPU 730 can be a digital signal processor, an FPGA, an ASIC, a PLA, a PLD, or a CPLD. Further, the CPU 730 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 7, the data processing system 700 can include that the SB/ICH 720 is coupled through a system bus to an I/O Bus, a read only memory (ROM) 756, universal serial bus (USB) port 764, a flash binary input/output system (BIOS) 768, and a graphics controller 758. PCI/PCIe devices can also be coupled to SB/ICH 788 through a PCI bus 762.

The PCI devices may include, for example, Ethernet adapters, add-in cards, and PC cards for notebook computers. The Hard disk drive 760 and CD-ROM 766 can use, for example, an integrated drive electronics (IDE) or serial advanced technology attachment (SATA) interface. In one implementation the I/O bus can include a super I/O (SIO) device.

Further, the hard disk drive (HDD) 760 and optical drive 766 can also be coupled to the SB/ICH 720 through a system bus. In one implementation, a keyboard 770, a mouse 772, a parallel port 778, and a serial port 776 can be connected to the system bus through the I/O bus. Other peripherals and devices that can be connected to the SB/ICH 720 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

The functions and features described herein may also be by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for interactive three-dimensional (3D) visualization of ultrasound images of a supraspinatus tendon injury, comprising:
acquiring a plurality of ultrasound images of a region in which the supraspinatus tendon injury is suspected;
preprocessing the plurality of ultrasound images, thus generating a plurality of preprocessed ultrasound images composed of pixels;
minimizing an energy of the plurality of preprocessed ultrasound images, thus generating a plurality of low energy preprocessed ultrasound images;
extracting, from the plurality of low energy preprocessed ultrasound images, a set of supraspinatus tendon images;
performing a morphological operation on the set of supraspinatus tendon images, thus generating a smoothed set of supraspinatus tendon images;
applying a binary mask to the smoothed set of supraspinatus tendon images to detect boundary points of the supraspinatus tendon, thus generating a set of segmented image frames;
arranging the set of segmented image frames based on a spatial position of each segmented image frame with respect to the supraspinatus tendon;
reconstructing a 3D representation of the supraspinatus tendon; and
rendering the 3D representation of the supraspinatus tendon on a display.

2. The method of claim 1, comprising acquiring the plurality of ultrasound images by:
isolating a shoulder region in which the supraspinatus tendon injury is suspected;
imaging the shoulder region by a high frequency ultrasound probe and generating a plurality of timestamped ultrasound images;
storing the plurality of timestamped ultrasound images in a database; and
retrieving a time series of the plurality of timestamped ultrasound images from the database.

3. The method of claim 1, further comprising:
preprocessing the plurality of ultrasound images by applying statistically adaptive contrast enhancement and speckle removal.

4. The method of claim 1, further comprising:
minimizing the energy of each of the plurality of preprocessed ultrasound images by applying an evolutionary algorithm.

5. The method of claim 4, wherein the evolutionary algorithm is a Darwinian particle swarm optimization.

6. The method of claim 1, further comprising:
extracting the set of supraspinatus tendon images by applying a segmentation algorithm.

7. The method of claim 6, wherein the segmentation algorithm is an enhanced Chan-Vese algorithm.

8. The method of claim 1, further comprising:
applying the binary mask by setting the pixels in the smoothed set of supraspinatus tendon images to zero when a corresponding pixel in the binary mask is zero; and
detecting the boundary points by comparing each remaining pixel to an edge point of the binary mask.

9. The method of claim 1, further comprising:
arranging the set of segmented image frames based on the spatial position by image registration.

10. The method of claim 1, comprising reconstructing the 3D representation of the supraspinatus tendon by:
applying an enhanced marching cubes operation on the set of segmented image frames to remove duplicate vertices and smooth surface and boundaries, thus generating an enhanced set of segmented image frames;
forming a 3D mesh of the enhanced set of segmented image frames; and
forming a patched 3D mesh by filling in open areas of the 3D mesh with pixels having an intensity equal to that of a neighboring pixel.

11. The method of claim 10, further comprising:
smoothing the patched 3D mesh by z-buffer rendering.

12. A system for interactive three-dimensional (3D) visualization of ultrasound images of a supraspinatus tendon injury, comprising:
a high frequency ultrasound probe configured to image a region in which the supraspinatus tendon injury is suspected, and generate a plurality of ultrasound images composed of pixels;
a database configured to store the plurality of ultrasound images;
a display;
a computing device operatively connected to the database and the display, the computing device including circuitry and a non-transitory computer readable medium having instructions stored therein that, when executed by one or more processors:
acquire the plurality of ultrasound images from the database;
preprocess the plurality of ultrasound images to generate a plurality of preprocessed ultrasound images;
minimize an energy of the plurality of preprocessed ultrasound images to generate a plurality of low energy preprocessed ultrasound images;
extract, from the plurality of low energy preprocessed ultrasound images, a set of supraspinatus tendon images;
perform a morphological operation on the set of supraspinatus tendon images to generate a smoothed set of supraspinatus tendon images;
apply a binary mask to the smoothed set of supraspinatus tendon images to detect boundary points of the supraspinatus tendon to generate a set of segmented image frames; arrange the set of segmented image frames based on a spatial position of each segmented image frame with respect to the supraspinatus tendon;
reconstruct a 3D representation of the supraspinatus tendon; and
render the 3D representation of the supraspinatus tendon on the display.

13. The system of claim 12, wherein the computing device is configured to preprocess the plurality of ultrasound images by applying statistically adaptive contrast enhancement and speckle removal.

14. The system of claim 12, wherein the computing device is configured to minimize the energy of each of the plurality of preprocessed ultrasound images by applying an evolutionary algorithm.

15. The system of claim 14, wherein the evolutionary algorithm is a Darwinian particle swarm optimization.

16. The system of claim 12, wherein the computing device is configured to extract the set of supraspinatus tendon images by applying a segmentation algorithm.

17. The system of claim 16, wherein the segmentation algorithm is an enhanced Chan-Vese algorithm.

18. The system of claim 12, wherein the computing device is configured to:
apply the binary mask by setting the pixels in the smoothed set of supraspinatus tendon images to zero when a corresponding pixel in the binary mask is zero; and
detect the boundary points by comparing each remaining pixel to an edge point of the binary mask.

19. The system of claim 12, wherein the computing device is configured to:
apply an enhanced marching cubes operation on the set of segmented image frames to remove duplicate vertices and smooth surface and boundaries to generate an enhanced set of segmented image frames;
form a 3D mesh of the enhanced set of segmented image frames;
form a patched 3D mesh by filling in open areas of the 3D mesh with pixels having an intensity equal to that of a neighboring pixel; and
smooth the patched 3D mesh by z-buffer rendering to generate a reconstruction of the 3D representation of the supraspinatus tendon.

20. A method for interactive three-dimensional (3D) visualization of ultrasound images of a supraspinatus tendon injury, comprising:
acquiring a plurality of ultrasound images of a region in which the supraspinatus tendon injury is suspected by isolating a shoulder region in which the supraspinatus tendon injury is suspected, imaging the shoulder region by a high frequency ultrasound probe, and storing a plurality of timestamped ultrasound images composed of pixels;
preprocessing the plurality of ultrasound images by applying statistically adaptive contrast enhancement and speckle removal, thus generating a plurality of preprocessed ultrasound images;
minimizing an energy of the plurality of preprocessed ultrasound images by applying an evolutionary algorithm, wherein the evolutionary algorithm is a Darwinian particle swarm optimization, thus generating a plurality of low energy preprocessed ultrasound images;
extracting, from the plurality of low energy preprocessed ultrasound images, a set of supraspinatus tendon images by applying a segmentation algorithm, wherein the segmentation algorithm is an enhanced Chan-Vese algorithm;
performing a morphological operation on the set of supraspinatus tendon images, thus generating a smoothed set of supraspinatus tendon images;
applying a binary mask to the smoothed set of supraspinatus tendon images to detect boundary points of the supraspinatus tendon by setting the pixels in the smoothed set of supraspinatus tendon images to zero when a corresponding pixel in the binary mask is zero and detecting boundary points by comparing each remaining pixel to an edge point of the binary mask, thus generating a set of segmented image frames;
arranging the set of segmented image frames based on a spatial position of each segmented image frame with respect to the supraspinatus tendon by image registration;
reconstructing a 3D representation of the supraspinatus tendon by applying an enhanced marching cubes operation on the set of segmented image frames to remove duplicate vertices and smooth surface and boundaries, thus generating an enhanced set of segmented image frames, forming a 3D mesh of the enhanced set of segmented image frames, forming a patched 3D mesh by filling in open areas of the 3D mesh with pixels having an intensity equal to that of a neighboring pixel; and rendering the 3D representation of the supraspinatus tendon on a display.

\* \* \* \* \*